United States Patent [19]
DeBusk

[11] Patent Number: 5,792,128
[45] Date of Patent: *Aug. 11, 1998

[54] ABSORBENT ARTICLE HAVING A RADIOPAQUE ELEMENT EMBEDDED IN A SIDE EDGE THEREOF AND METHOD FOR MAKING SAME

[75] Inventor: Autry O. V. DeBusk, Powell, Tenn.

[73] Assignee: DeRoyal Industries, Inc., Powell, Tenn.

[ * ] Notice: The term of this patent shall not extend beyond the expiration date of Pat. No. 5,575,781.

[21] Appl. No.: 640,486

[22] Filed: May 1, 1996

Related U.S. Application Data

[63] Continuation-in-part of Ser. No. 539,677, Oct. 5, 1995, Pat. No. 5,575,781.

[51] Int. Cl.⁶ .............................. A61F 13/15; A61F 13/20
[52] U.S. Cl. ................................................... 604/362
[58] Field of Search ................................. 604/358, 362, 604/385.1; 602/41–43

[56] References Cited

U.S. PATENT DOCUMENTS

| | | | |
|---|---|---|---|
| 2,698,270 | 12/1954 | Mesek | 154/93 |
| 3,097,649 | 7/1963 | Gray | 604/362 |
| 3,301,257 | 1/1967 | Crowe, Jr. et al. | 128/296 |
| 3,422,816 | 1/1969 | Robinson et al. | 604/362 |
| 3,464,415 | 9/1969 | Brownlee | 128/296 |
| 3,698,393 | 10/1972 | Stone | 604/362 |
| 3,911,922 | 10/1975 | Kliger | 604/369 |
| 3,965,907 | 6/1976 | Hardy et al. | 128/296 |
| 4,205,680 | 6/1980 | Marshall | 128/296 |

*Primary Examiner*—John G. Weiss
*Assistant Examiner*—Ki Yong O
*Attorney, Agent, or Firm*—Paul E. Hodges, P.C.

[57] ABSTRACT

An absorbent article in the form of a closely-woven single-layered fabric sheet which has incorporated therein an elongated radiopaque thread embedded in multiple folds along at least one edge of the sheet. The radiopaque element preferably is unattached to the fabric, but rather is mechanically captured within a first fold that is further folded inwardly of and onto the top surface of the fabric sheet. The fabric sheet is woven of absorbent yarns and in a weave pattern which produces a tight weave such that the article is suitable for use as a drape in a surgical procedure, or in the nature of a laparotomy sponge. A method for the manufacture of the absorbent article is disclosed.

11 Claims, 4 Drawing Sheets

WEAVE PATTERN
BODY: EIGHT HARNESS

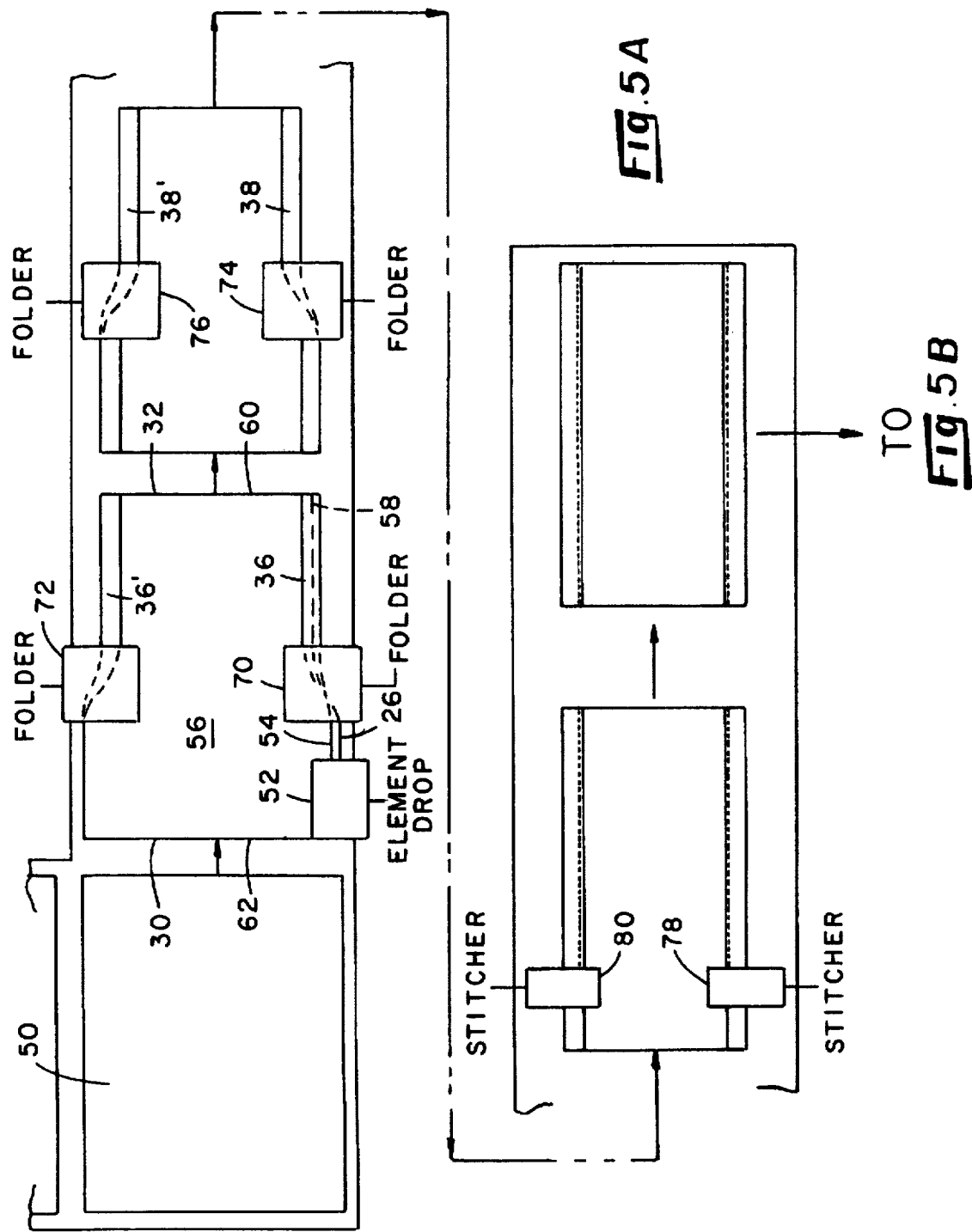

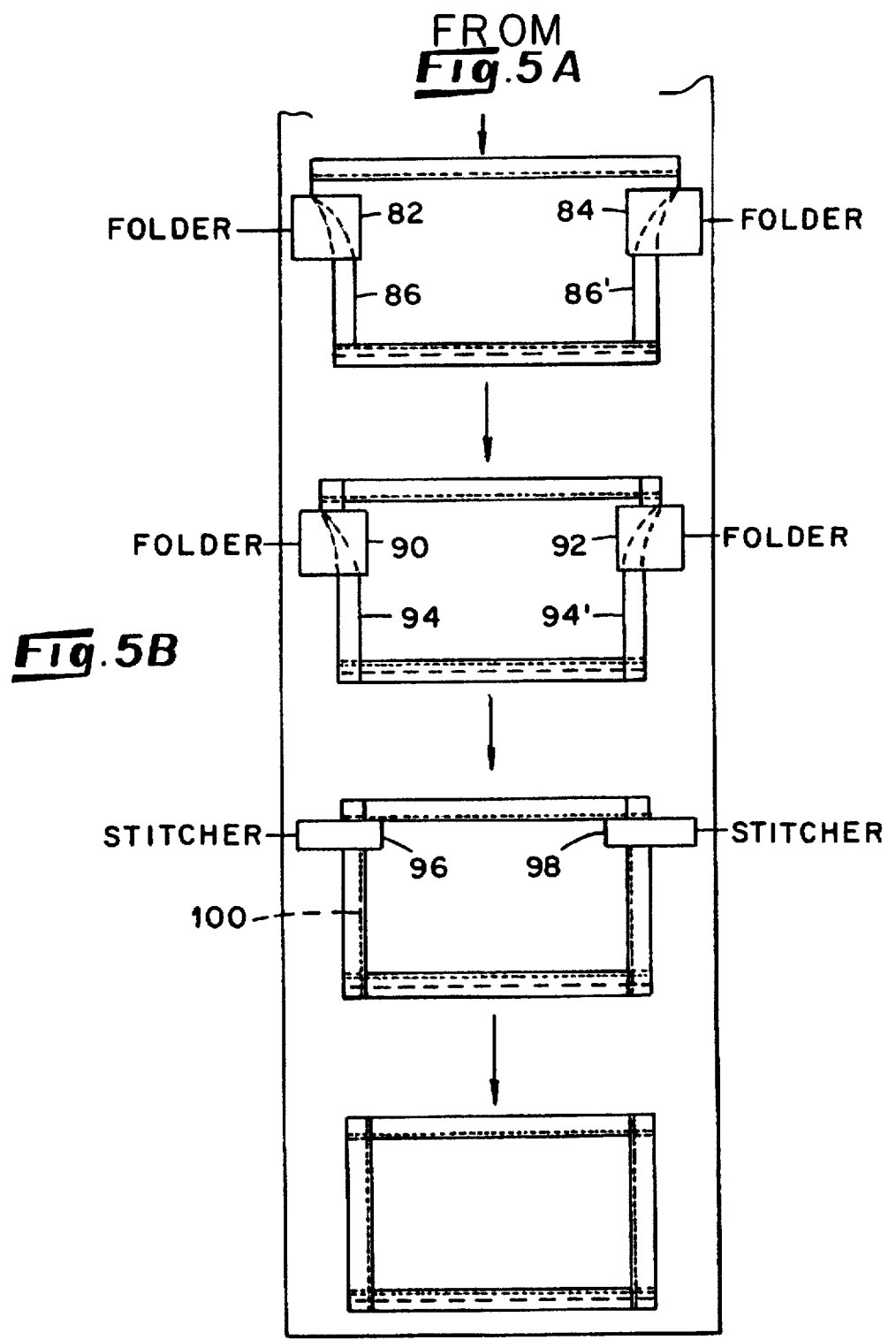

ABSORBENT ARTICLE HAVING A RADIOPAQUE ELEMENT EMBEDDED IN A SIDE EDGE THEREOF AND METHOD FOR MAKING SAME

This application is a continuation-in-part of commonly owned application Ser. No. 08/539,677 filed Oct. 5, 1995, now U.S. Pat. No. 5,575,781, entitled: ABSORBENT ARTICLE USEFUL IN MEDICAL APPLICATIONS.

FIELD OF INVENTION

This invention relates to absorbent articles which are used in the course of administering medical care to a patient, and particularly to an absorbent article useful in surgical procedures and the methods for their manufacture.

BACKGROUND OF INVENTION

Heretofore the laparotomy sponge has served as the basic absorbent article used in medical applications, particularly surgical operations, for absorbing body fluids, especially blood. Laparotomy sponges most commonly comprise a plurality of layers of absorbent loosely-woven gauze which are bound to one another along the side edges of the overlying layers of gauze. The general theory behind the use of multilayered gauze in laparotomy sponges is that the openness of the weave of the gauze, plus the bulk provided by the multiple layers permits the sponge to rapidly take up substantial volumes of body fluids. In actual practice, however, it has been found that and individual one of the common laparotomy sponges takes up only a relatively small portion of the total volume of fluids that are present in a surgical procedure, so that in a given surgical procedure, for example, there will be a large number of laparotomy sponges used. In today's medical environment, laparotomy sponges are disposed of after a single use, thereby bringing into question the practice of using large numbers of single use laparotomy sponges. Of recent, and in part due to attempts to reduce medical care costs, the yarn counts and the denier of the yarns employed in the weaving of the gauze employed in laparotomy sponges has tended to be reduced in attempts to reduce the cost of these sponges. These actions have reduced the absorptive capacity of these sponges so that more sponges are being required to perform a given surgical procedure than was required when using prior sponges.

A vast majority of laparotomy sponges are used in surgical procedures for absorbing body fluids, for wiping and cleaning a patient, for packing body organs while the organs are exposed outside the patient's body cavity (after the sponge has been soaked in saline solution) to protect the organs from drying out, and for other similar uses. In many instances, the sponges are inserted into the patient's body cavity to aid in keeping a surgical field clear for the surgeon to perform a surgical procedure within the body cavity. As is well recognized in the art, a gauze laparotomy sponge, when soaked with blood, very strikingly resembles normal body tissue found within a patient's body cavity. As a consequence, all surgical procedures require strict adherence to accounting for laparotomy sponges (and other sponge types) during a surgical procedure. Further, all laparotomy sponges used in surgical procedures are provided with at least one radiopaque element which is in some manner incorporated into the structure of the sponge so as to ensure its integrity with the sponge during use of the sponge. This radiopaque element is intended to be readily detectable under X-ray examination. If, after completion of a surgical procedure, all sponges can not be accounted for, the patient is examined by X-ray equipment in an attempt to ensure that a "missing" sponge has not been left in the patient's body cavity.

Heretofore, surgical towels, comprising a woven cotton fabric, have been used in draping off a sterile field within which a surgeon is to perform a surgical procedure. This function of the towel is to assist in maintaining a sterile field by ensuring that bacteria, etc. on the patient's body are not transferred away from the body and possibly into the patient's body cavity during the time when the body cavity is open for performance of the surgical procedure or the like, and to absorb any body fluids which may escape from the open body cavity in the course of the surgical procedure. To successfully perform these functions, the towel is commonly a single-layered, woven, cotton fabric. The weave of the fabric is a tight weave, that is, there is a relatively large number of yarns per inch in the weave and the yarns are closely packed in the weave. Because towels do not include a radiopaque element in their structure, they are not acceptable for use inside a patient's body cavity.

Heretofore, many attempts have been made to devise ways to incorporate a radiopaque element in the structure of absorbent articles that may be disposed temporarily inside a patient's body cavity during a surgical procedure. These attempts have included weaving one or more radiopaque yarns into the weave pattern of the fabric from which the absorbent article is formed. Because radiopaque yarns are extensible and have less breaking strength than cotton yarns, for example, they are not amenable to weaving techniques, and this procedure has not been successful. Another attempt has been to loosely lay a radiopaque yarn into a weave pattern, or to lay the yarn loosely between layers of gauze. Such loose radiopaque yarns, however, are not adequately secured within the absorbent article and pose the danger of escape of the yarn or a broken portion thereof into a patient's body cavity. Radiopaque yarns have also been incorporated into a loop which is secured to one edge of an absorbent article. In this construction, there remains the danger of all or a portion of the yarn escaping from the loop during using of the absorbent article. Heretofore, there has been no known successful means for including a radiopaque element in a surgical towel, hence surgical towels currently remain a separate supply item in surgical procedures, as do laparotomy sponges, since these two products presently serve different functions.

In view of the problems attending the prior art, it is an object of the present invention to provide an absorbent article which may be used alternatively as a drape or as a laparotomy sponge during a surgical procedure.

It is another object to provide a novel absorbent article useful in surgical procedures in which there is securely incorporated a radiopaque element and wherein the presence of the radiopaque element does not detract from the use of the absorbent article for draping, absorption, wiping and similar uses.

BRIEF DESCRIPTION OF THE DRAWINGS

Other objects and advantages of the present invention will be recognized by one skilled in the art and in view of the present disclosure, including the claims and drawings in which:

FIG. 2 is a sectional view taken generally along the line 2—2 of FIG. 1;

SUMMARY OF INVENTION

In accordance with the present invention there is provided an absorbent article in form of a close-weave woven single-layered fabric sheet which has incorporated therein in a radiopaque thread embedded in multiple folds along one side edge of the fabric sheet. The radiopaque thread preferably is unattached to the fabric, but rather is mechanically captured within the multiple folds. The fabric of the present invention is woven in a pattern which produces a close or tight weave, i.e. having a relatively large number of yarns per inch of fabric length and width such that the article is suitable for use as a draping fabric in a surgical procedure, and further, is suitable for use in the nature of a laparotomy sponge. Preferably the absorbent article is of a huck weave construction of 74×28 with 20/1 cotton warp yarns and 8/1 cotton weft yarns thereby providing a preferred finished nonwashed weight of a 17"×29" fabric sheet of at least 0.1300 grams per in$^2$. Each side edge of the fabric sheet preferable is twice-folded inwardly of and onto a surface of the body of the fabric sheet, each fold being about ½ inch in width. The radiopaque thread is laid within the first fold so that when the side edge is folded a second time, the radiopaque thread is fully encapsulated internally of the multiple folds. Folding of the end edges of the fabric sheet serves to close the opposite ends of each folded side edge thereby preventing escape of the radiopaque thread from the open ends of that folded side edge within which the thread is incorporated. A method for the manufacture of the absorbent product is disclosed and claimed.

DETAILED DESCRIPTION OF INVENTION

Figure 1:
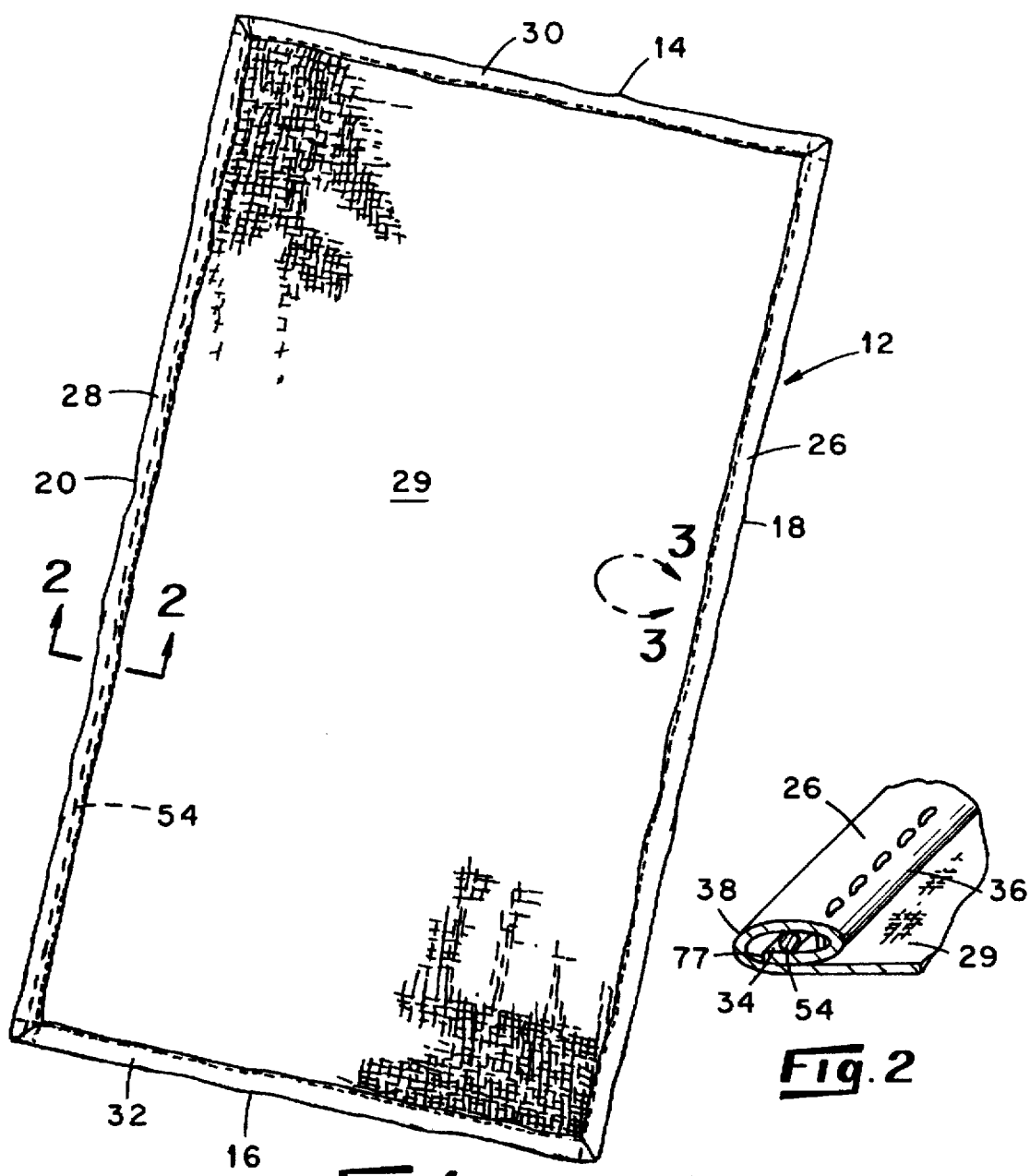
FIG. 1 is a perspective representation of an absorbent article embodying various of the features of the present invention.

With reference to FIG. 1, there is depicted one embodiment of an absorbent article according to the present invention comprising a fabric sheet 12 having a length dimension that extends between opposite ends 14 and 16 thereof and a width dimension that extends between opposite sides 18 and 20 thereof. The fabric sheet is folded multiple times inwardly along each of its side and end edges, the side edges being designated 26 and 28 and the end edges being designated 30 and 32. Referring also to FIG. 2, the multiple folds of each side edge are formed by folding a first side edge portion 34 inwardly of the fabric sheet to form a first fold 36 and thereafter folding the first fold inwardly of the fabric sheet to form a second fold 38 and thereby define a twice-folded side edge 26, for example, along each side edge of the fabric sheet.

The fabric sheet of the present invention, being intended to serve either as an absorbent for body fluids or other fluids occasioned in the course of a surgical procedure, or as a protective barrier about the periphery of a surgical operative site, is constructed from an absorbent material which also is suitable for conversion into a sheet that is sufficiently dense as will provide suitable protection against the transfer of bacteria through the thickness thereof when the absorbent article is employed in a draping mode. In a preferred embodiment, the fabric sheet is formed as a woven fabric. The yarns employed in the weaving of the fabric preferably are cotton yarns, but other absorbent yarn materials or absorbent yarns formed of a combination of materials may be employed. In any event, the yarns must be suitable for introduction into the body cavity of a surgical patient in the course of a surgical procedure. Among other things, this requires that the yarns do not shed yarn fragments during use such as might become lodged within a body cavity and initiate the formation of granulomas. Whereas the yarns of the resultant woven fabric may be bleached or dyed, the dye employed must be a fast dye and the bleaching or dying process, and/or the dye employed, must be of a type acceptable for use in fabrics that may enter the body cavity of a patient. Suitable dyes are well known in the art.

Figure 3:
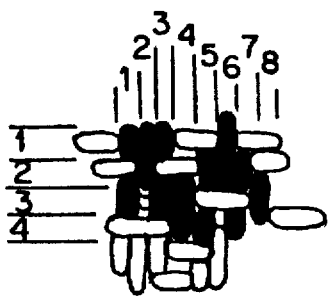
FIG. 3 is a schematic representation of a huck weave pattern.
Figure 4A:
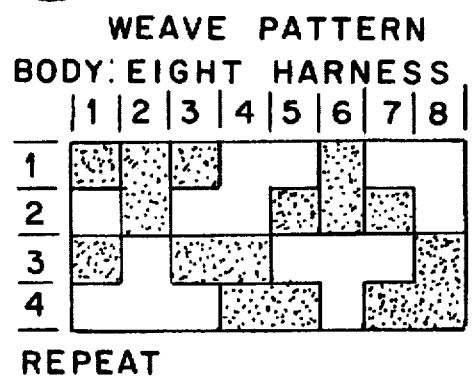
FIGS. 4A and 4B are diagrams depicting one embodiment of a loom setup for producing a huck weave pattern of the absorbent article of the present invention; and, FIGS. 5A and 5B present a schematic representation of an apparatus for use in the manufacture of the present absorbent article.
Figure 4B:
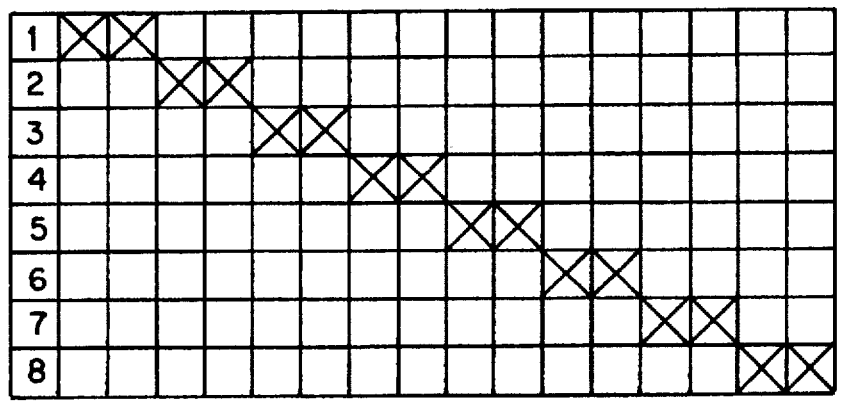

One suitable weave pattern for the construction of the absorbent article of the present invention is depicted in FIG. 3. A typical loom setup for producing the weave pattern of FIG. 3 is depicted in FIGS. 4A and 4B. The depicted weave pattern is a huck weave. In this weave pattern, each repeat, employing an eight harness arrangement on a loom, comprises eight warp yarns and four weft yarns. In this pattern, there is provided one draw per eye, two per dent, and a reed setup of 35.15 dents per inch, as depicted in FIGS. 4A and 4B. The warp yarns preferred in the present absorbent article are each of a 20/1 construction, i.e. 20 denier weight and a single yarn. The weft yarns preferred are each of 8/1 construction. Further, in a preferred embodiment, there are 78 warp yarns per inch of width of the fabric and 28 weft yarns per inch of width of the fabric.

The radiopaque element of the present woven absorbent product preferably comprises a thread formed from polyvinyl chloride filled with at least about 60%, by weight, of USP barium sulfate, as further specified in Federal Specification DDD-P-46D, paragraphs 4.5.4 and 3.3.1, as revised May 7, 1968. The preferred thread has a diameter of about 0.025 inch, ±0.003 inch, with a yield of about 2500 feet per pound of thread. The elongation of the thread preferably does not exceed about 300%. Less preferred, but acceptable in certain applications, is an elongated radiopaque element comprising a flat narrow ribbon of polyvinyl chloride containing barium sulfate.

A woven absorbent product in accordance with the present invention is about 17 inches in width and about 29 inches in length, after hemming. When cotton yarns are employed in the manufacture of the fabric sheet, the woven product is washed to remove oils and/or foreign matter from the product and thereby soften the feel of the product and enhance its rate of absorptivity. This washing of a woven cotton absorbent product results in shrinkage of the product by between about 5 and 10 percent. A preferred woven absorbent product weighs about 0.1300 grams/in$^2$ prior to washing and about 0.1592 gm/in$^2$ after washing.

FIGS. 5A and 5B depict schematically one embodiment of an apparatus for use in the manufacture of the present woven absorbent product. Employing the depicted apparatus, a woven fabric sheet 50 is fed forwardly past an element drop 52 where a length of radiopaque thread 54 is overlaid on the top surface 56 of one side edge 26 of the sheet. The leading end 58 of the thread is overlaid at the leading edge 60 of the fabric sheet as the sheet is moved forwardly beneath the element drop 52. As the fabric sheet is further moved forwardly beneath the element drop 52, the radiopaque thread is continued to be fed onto the top surface of the fabric sheet. As the trailing edge 62 of the fabric sheet passes beneath the element drop, the thread is severed, thereby providing a length of radiopaque thread which extends substantially fully between the opposite ends 30 and 32 of the fabric sheet.

The fabric sheet with the radiopaque thread disposed along one of its side edges is fed forwardly between and through first and second folders 70 and 72 whereupon each of the side edges 26 and 28 are folded inwardly and onto the top surface 29 of the fabric sheet to form first folds 36 and 36'. This first folding action captures the radiopaque thread within the first fold as best seen in FIG. 1 and 2. Thereupon, the fabric sheet in fed forwardly between and through third and fourth folders 74 and 76 whereupon the first folds of each of the side edges of the fabric sheet are again folded inwardly and onto the top surface of the fabric sheet to form second folds 38 and 38'. This second fold serves to cause the raw side edge 77 of the fabric sheet to be captured inside the second fold so that no cut ends of yarns are exposed externally of the product.

Following completion of the second folds along the opposite side edges of the fabric sheet, the fabric sheet is fed forwardly between and through first and second stitchers 78 and 80 where the first and second folds are stitched by stitches 81, to the body of the fabric sheet to secure the folds in their folded condition. In a preferred stitching operation, the first and second folds are stitched to the body of the fabric sheet using a cotton thread and at least eight stitches per linear inch of stitching.

Thereafter, the fabric sheet with its opposite side edges stitched, is fed laterally of its original forward direction into, between and through fifth and sixth folders 82 and 84 where the ends 30 and 36 of the fabric sheet are folded inwardly and onto the top surface of the body of the fabric sheet to define first end folds 86 and 86'. The fabric sheet thereupon is fed forwardly between and through seventh and eighth folders 90 and 92 where the first end folds 86 and 86' are folded inwardly and onto the top surface of the body of the fabric sheet to form second end folds 94 and 94'. The thus folded fabric sheet is thereupon fed between and through third and fourth stitchers 96 and 98 where the first and second end folds along each of the opposite ends of the fabric sheet are stitched, by stitches 100, to the body of the fabric sheet to secure the folds in position as described hereinabove in connection with the formation of the side edge folds.

It will be apparent that a radiopaque element may be included in more than one of the folded side edges of the fabric sheet, but such is not required. Further, the radiopaque element may be provided along an end edge of the fabric sheet, in lieu of providing the radiopaque element along a side edge.

Still further, the fabric sheet of the present invention may be woven with one or more selvedge edges which may not require folding thereof inwardly of the body of the fabric sheet, inasmuch as selvedge edges do not include cut ends of yarns or loose yarns.

Accordingly, the method of the present invention for the fabrication of an absorbent product useful in medical applications comprises the steps of (a) providing a single-layered woven fabric sheet having a weave pattern which is sufficiently tight as permits the fabric sheet to be used as an effective barrier in establishing a sterile field about a surgical site when the fabric sheet is used as surgical drape, said woven fabric sheet including first and second sides and first and second ends, and a top surface, (b) disposing an elongated radiopaque element on said top surface of said fabric sheet and aligned along one of said first and second sides or one of said first and second ends of said fabric sheet, (c) folding that end or side of said fabric sheet along which said radiopaque element is disposed inwardly and onto said top surface of said fabric sheet to define a first fold within which said radiopaque element is captured, (d) thereafter, folding said first fold inwardly and onto said top surface of said fabric sheet to define a second fold, and (e) securing said first and second folds to said top surface of said fabric sheet with said radiopaque element captured within said folds.

Notably, the formation of the end folds also serves to cover the opposite ends of the radiopaque element, thereby preventing the escape or withdrawal of the radiopaque element from its covering folds and preventing either end of the radiopaque element from projecting from the absorbent product where an end could present a possible source of irritation to a patient, especially with the product is used to absorb fluids from an incision, open wound or the like.

The absorbent product of the present invention possesses the barrier properties required of a surgical drape in establishing and maintaining a sterile field adjacent a surgical site, and the absorptive properties of a surgical sponge, employing only a single layer of woven fabric as opposed to the multiple layers of laparotomy sponges, for example. The presence of the radiopaque element secured along one side edge of the absorbent product provides a means by which the product can be identified through X-ray examination. Further, being of an elongated geometry, i.e. a thread, it is virtually impossible for the element to become "bunched up" and thereby escape detection by X-ray examination as occurs in certain prior art sponges. Incorporation of the radiopaque element into the present absorbent product effectively permits the present product to be employed alternatively as either a surgical drape or a surgical sponge, thereby permitting a health care institution or facility to order and stock a single absorbent product which can be used either as a surgical drape or as a surgical sponge. Further, the quantity of absorbent material present in the present product is greater than the quantity of absorbent material of a common surgical sponge, thereby permitting the use of fewer absorbent products per medical procedure.

Whereas the present absorbent product has been described herein in specific terms and embodiments, it will be recognized by one skilled in the art that alternatives exist in the construction and fabrication of the present product and it is intended that the invention be limited only as set forth in the claims appended hereto.

What is claimed:

1. An absorbent product useful in medical applications comprising
   a fabric sheet including tightly-woven absorbent yarns, and including first and second opposite side edges and first and second opposite end edges, and a top surface,
   an elongated radiopaque element disposed along at least one of said first and second side edges or said first and second end edges,
   that side or end edge of said fabric sheet along which said elongated radiopaque element is disposed being folded inwardly of and onto the top surface of said fabric sheet to define a first fold within which said radiopaque element is captured, and thereafter said first fold being further folded inwardly of and onto the top surface of said fabric sheet to define a second fold within which said first fold and said radiopaque element are captured, thereby leaving the major portion of said fabric sheet as an unfolded single layer, and
   means securing said first and second folds in their folded positions to said top surface of said fabric sheet.

2. The absorbent product of claim 1 wherein said absorbent yarns comprise cotton.

3. The absorbent product of claim 1 wherein said fabric sheet includes width and length dimensions and the weave pattern of said woven fabric sheet includes a sufficient number of yarns per linear inch of width and length of said fabric sheet as will develop an effective barrier for maintaining a sterile field about a surgical site when said absorbent product is employed as a drape.

4. The absorbent product of claim 1 wherein the weave pattern thereof is a huck weave pattern.

5. The absorbent product of claim 1 and including one or more further folded side or end edges of said fabric sheet and one or more elongated radiopaque elements disposed in one or more of said further folded side or end edges of said fabric sheet.

6. The absorbent product of claim 1 wherein said radiopaque element is disposed within multiple folds defined by one of said first and second side edges, and wherein said of said first and second end edges are each folded inwardly and onto said top surface of said fabric sheet to close the opposite ends of the folds of that one of said first and second side edges within which said radiopaque element is disposed.

7. The absorbent product of claim 1 wherein said radiopaque element includes polyvinyl chloride having barium sulfate incorporated therein.

8. A method for the fabrication of an absorbent product useful in medical applications comprising the steps of providing a single layer of woven fabric sheet having a weave pattern which is sufficiently tight as permits the fabric sheet to be used as an effective barrier in establishing a sterile field about a surgical site when the fabric sheet is used as surgical drape, said layer of woven fabric sheet including first and second side edges and first and second end edges, and a top surface, disposing an elongated radiopaque element on said top surface of said fabric sheet and aligned along one of said first and second side edges of one of said first and second end edges of said layer of fabric sheet, folding that end or side edge of said layer of fabric sheet along which said radiopaque element is disposed inwardly and onto said top surface of said layer of fabric sheet to define a first fold within which said radiopaque element is captured, thereafter, folding said first fold inwardly and onto said top surface of said layer of fabric sheet to define a second fold, leaving a major portion of said layer of fabric sheet unfolded, and securing said first and second folds to said top surface of said layer of fabric sheet with said radiopaque element captured within said folds.

9. The method of claim 8 and including the step of folding inwardly of and onto the top surface of said fabric sheet at least two of said side or end edges of said fabric sheet to close the opposite open ends of that fold within which said radiopaque element is disposed.

10. The method of claim 8 wherein said step of securing said first and second folds to said top surface includes stitching of said folds to said top surface.

11. The method of claim 8 and including the step of washing said absorbent product.

* * * * *